(12) United States Patent
Hur et al.

(10) Patent No.: US 8,765,420 B2
(45) Date of Patent: Jul. 1, 2014

(54) METHOD FOR PREPARING PTEROCARPAN

(75) Inventors: Hor-Gil Hur, Gwangju (KR); Jae Hong Han, Suwon-si (KR); Ji-Young Seo, Gwangju (KR)

(73) Assignee: Gwangju Institute of Science and Technology, Buk-Gu, Gwangju (KR)

( * ) Notice: Subject to any disclaimer, the term of this patent is extended or adjusted under 35 U.S.C. 154(b) by 0 days.

(21) Appl. No.: 13/636,931

(22) PCT Filed: Aug. 31, 2010

(86) PCT No.: PCT/KR2010/005891
§ 371 (c)(1),
(2), (4) Date: Sep. 24, 2012

(87) PCT Pub. No.: WO2011/118887
PCT Pub. Date: Sep. 29, 2011

(65) Prior Publication Data
US 2013/0130332 A1    May 23, 2013

(30) Foreign Application Priority Data
Mar. 25, 2010    (KR) .................. 10-2010-0027000

(51) Int. Cl.
*C12P 17/02*    (2006.01)

(52) U.S. Cl.
USPC .................................................. 435/123

(58) Field of Classification Search
None
See application file for complete search history.

*Primary Examiner* — Nashaat Nashed
(74) *Attorney, Agent, or Firm* — Nath, Goldberg & Meyer; Joshua B. Goldberg

(57) ABSTRACT

The present invention relates to a novel method for preparing pterocarpan from isoflavan-4-ol.

With the use of the method of the present invention, the absolute configuration of C3 and C4 positions on the B-ring of isoflavan-4-ols is maintained identically also in pterocarpans, and thus, enantiopure pterocarpans can be efficiently prepared.

6 Claims, 18 Drawing Sheets

SEQUENCE LISTING

```
<160> NUMBER OF SEQ ID NOS: 3

<210> SEQ ID NO 1
<211> LENGTH: 1377
<212> TYPE: DNA
<213> ORGANISM: Pseudomonas pseudoalcaligenes
<220> FEATURE:
<223> OTHER INFORMATION: strain KF707, Biphenyl dioxygenase

<400> SEQUENCE: 1
atgagctcat caatcaaaga agtgcaggga gcccctgtga agtgggttac caattggacg      60
ccggaggcga tccgggggtt ggtcgatcag gaaaaagggc tgcttgatcc acgcatctac     120
gccgatcaga gtctttatga gctggagctt gagcgggttt ttggtcgctc ttggctgtta     180
cttgggcacg agagtcatgt gcctgaaacc ggggacttcc tggccactta catgggcgaa     240
gatccggtgg ttatggtgcg acagaaagac aagagcatca aggtgttcct gaaccagtgc     300
cggcaccgcg gcatgcgtat ctgccgctcg gacgccggca acgccaaggc tttcacctgc     360
agctatcacg gctgggccta cgacatcgcc ggcaagctgg tgaacgtgcc gttcgagaag     420
gaagcctttt gcgacaagaa agaaggcgac tgcggctttg acaaggccga atggggcccg     480
ctccaggcac gcgtggcaac ctacaagggc ctggtctttg ccaactggga tgtgcaggcg     540
ccagacctgg agacctacct cggtgacgcc cgccctata tggacgtcat gctggatcgc     600
acgccggccg ggactgtggc catcggcggc atgcagaagt gggtgattcc gtgcaactgg     660
aagtttgccg ccgagcagtt ctgcagtgac atgtaccacg ccggcaccac gacgcacctg     720
```

```
tccggcatcc tggcgggcat tccgccggaa atggacctct cccaggcgca gatacccacc    780
aagggcaatc agttccgggc cgcttggggc gggcacggct cgggctggta tgtcgacgag    840
ccgggctcac tcctggcggt gatgggcccc aaggtcaccc agtactggac cgagggtccg    900
gctgccgagc ttgcggaaca gcgactgggc cacaccatgc cggttcgacg catgttcggc    960
cagcacatga gcgtcttccc gacctgctcg ttcctcccgg ccatcaacac catccggatc   1020
tggcacccgc gtggtcccaa tgaaatcgag gtgtgggcct tcaccctggt cgatgccgat   1080
gccccggccg agatcaagga agaatatcgc cggcacaaca tccgcacctt ctccgcaggc   1140
ggcgtgtttg agcaggacga tggcgagaac tgggtggaga tccagaaggg gctacgtggg   1200
tacaaggcca agagccagcc gctcaatgcc cagatgggcc tgggtcggtc gcagaccggt   1260
caccctgatt tcctggcaa cgtcggctac gtctacgccg aagaagcggc gcggggtatg   1320
tatcaccact ggatgcgcat gatgtccgag cccagctggg ccacgctcaa gccctga      1377
```

<210> SEQ ID NO 2
<211> LENGTH: 460
<212> TYPE: PRT
<213> ORGANISM: Rhodococcus sp. RHA1
<220> FEATURE:
<223> OTHER INFORMATION: Bipheny dioxygenase

<400> SEQUENCE: 2

```
Met Thr Asp Val Gln Cys Glu Pro Ala Leu Ala Gly Arg Lys Pro Lys
1               5                   10                  15

Trp Ala Asp Ala Asp Ile Ala Glu Leu Val Asp Glu Arg Thr Gly Arg
            20                  25                  30

Leu Asp Pro Arg Ile Tyr Thr Asp Glu Ala Leu Tyr Glu Gln Glu Leu
        35                  40                  45

Glu Arg Ile Phe Gly Arg Ser Trp Leu Leu Met Gly His Glu Thr Gln
    50                  55                  60

Ile Pro Lys Ala Gly Asp Phe Met Thr Asn Tyr Met Gly Glu Asp Pro
65                  70                  75                  80

Val Met Val Val Arg Gln Lys Asn Gly Glu Ile Arg Val Phe Leu Asn
                85                  90                  95

Gln Cys Arg His Arg Gly Met Arg Ile Cys Arg Ala Asp Gly Gly Asn
            100                 105                 110

Ala Lys Ser Phe Thr Cys Ser Tyr His Gly Trp Ala Tyr Asp Thr Gly
        115                 120                 125

Gly Asn Leu Val Ser Val Pro Phe Glu Glu Gln Ala Phe Pro Gly Leu
    130                 135                 140

Arg Lys Glu Asp Trp Gly Pro Leu Gln Ala Arg Val Glu Thr Tyr Lys
145                 150                 155                 160

Gly Leu Ile Phe Ala Asn Trp Asp Ala Asp Ala Pro Asp Leu Asp Thr
                165                 170                 175

Tyr Leu Gly Glu Ala Lys Phe Tyr Met Asp His Met Leu Asp Arg Thr
            180                 185                 190

Glu Ala Gly Thr Glu Ala Ile Pro Gly Ile Gln Lys Trp Val Ile Pro
        195                 200                 205

Cys Asn Trp Lys Phe Ala Ala Glu Gln Phe Cys Ser Asp Met Tyr His
    210                 215                 220

Ala Gly Thr Thr Ser His Leu Ser Gly Ile Leu Ala Gly Leu Pro Asp
225                 230                 235                 240

Gly Val Asp Leu Ser Glu Leu Ala Pro Pro Thr Glu Gly Ile Gln Tyr
```

```
                      245                 250                 255
Arg Ala Thr Trp Gly Gly His Gly Ser Gly Phe Tyr Ile Gly Asp Pro
            260                 265                 270

Asn Leu Leu Ala Ile Met Gly Pro Lys Val Thr Glu Tyr Trp Thr
        275                 280                 285

Gln Gly Pro Ala Ala Glu Lys Ala Ser Glu Arg Leu Gly Ser Thr Glu
        290                 295                 300

Arg Gly Gln Gln Leu Met Ala Gln His Met Thr Ile Phe Pro Thr Cys
305                 310                 315                 320

Ser Phe Leu Pro Gly Ile Asn Thr Ile Arg Ala Trp His Pro Arg Gly
                325                 330                 335

Pro Asn Glu Ile Glu Val Trp Ala Phe Thr Val Val Asp Ala Asp Ala
                340                 345                 350

Pro Glu Glu Met Lys Glu Glu Tyr Arg Gln Gln Thr Leu Arg Thr Phe
            355                 360                 365

Ser Ala Gly Gly Val Phe Glu Gln Asp Asp Gly Glu Asn Trp Val Glu
        370                 375                 380

Ile Gln Gln Val Leu Arg Gly His Lys Ala Arg Ser Arg Pro Phe Asn
385                 390                 395                 400

Ala Glu Met Gly Leu Gly Gln Thr Asp Ser Asp Asn Pro Asp Tyr Pro
                405                 410                 415

Gly Thr Ile Ser Tyr Val Tyr Ser Glu Glu Ala Ala Arg Gly Leu Tyr
                420                 425                 430

Thr Gln Trp Val Arg Met Met Thr Ser Pro Asp Trp Ala Ala Leu Asp
            435                 440                 445

Ala Thr Arg Pro Ala Val Ser Glu Ser Thr His Thr
        450                 455                 460

<210> SEQ ID NO 3
<211> LENGTH: 458
<212> TYPE: PRT
<213> ORGANISM: Pseudomonas pseudoalcaligenes
<220> FEATURE:
<223> OTHER INFORMATION: strain KF707, Biphenyl dioxygenase

<400> SEQUENCE: 3

Met Ser Ser Ser Ile Lys Glu Val Gln Gly Ala Pro Val Lys Trp Val
1               5                   10                  15

Thr Asn Trp Thr Pro Glu Ala Ile Arg Gly Leu Val Asp Gln Glu Lys
            20                  25                  30

Gly Leu Leu Asp Pro Arg Ile Tyr Ala Asp Gln Ser Leu Tyr Glu Leu
        35                  40                  45

Glu Leu Glu Arg Val Phe Gly Arg Ser Trp Leu Leu Leu Gly His Glu
    50                  55                  60

Ser His Val Pro Glu Thr Gly Asp Phe Leu Ala Thr Tyr Met Gly Glu
65                  70                  75                  80

Asp Pro Val Val Met Val Arg Gln Lys Asp Lys Ser Ile Lys Val Phe
                85                  90                  95

Leu Asn Gln Cys Arg His Arg Gly Met Arg Ile Cys Arg Ser Asp Ala
            100                 105                 110

Gly Asn Ala Lys Ala Phe Thr Cys Ser Tyr His Gly Trp Ala Tyr Asp
        115                 120                 125

Ile Ala Gly Lys Leu Val Asn Val Pro Phe Glu Lys Glu Ala Phe Cys
    130                 135                 140

Asp Lys Lys Glu Gly Asp Cys Gly Phe Asp Lys Ala Glu Trp Gly Pro
```

-continued

```
        145                 150                 155                 160
Leu Gln Ala Arg Val Ala Thr Tyr Lys Gly Leu Val Phe Ala Asn Trp
                    165                 170                 175

Asp Val Gln Ala Pro Asp Leu Glu Thr Tyr Leu Gly Asp Ala Arg Pro
                    180                 185                 190

Tyr Met Asp Val Met Leu Asp Arg Thr Pro Ala Gly Thr Val Ala Ile
            195                 200                 205

Gly Gly Met Gln Lys Trp Val Ile Pro Cys Asn Trp Lys Phe Ala Ala
            210                 215                 220

Glu Gln Phe Cys Ser Asp Met Tyr His Ala Gly Thr Thr His Leu
225                 230                 235                 240

Ser Gly Ile Leu Ala Gly Ile Pro Pro Glu Met Asp Leu Ser Gln Ala
                    245                 250                 255

Gln Ile Pro Thr Lys Gly Asn Gln Phe Arg Ala Ala Trp Gly Gly His
                    260                 265                 270

Gly Ser Gly Trp Tyr Val Asp Glu Pro Gly Ser Leu Leu Ala Val Met
                    275                 280                 285

Gly Pro Lys Val Thr Gln Tyr Trp Thr Glu Gly Pro Ala Ala Glu Leu
        290                 295                 300

Ala Glu Gln Arg Leu Gly His Thr Met Pro Val Arg Arg Met Phe Gly
305                 310                 315                 320

Gln His Met Ser Val Phe Pro Thr Cys Ser Phe Leu Pro Ala Ile Asn
                    325                 330                 335

Thr Ile Arg Ile Trp His Pro Arg Gly Pro Asn Glu Ile Glu Val Trp
                    340                 345                 350

Ala Phe Thr Leu Val Asp Ala Asp Ala Pro Ala Glu Ile Lys Glu Glu
                    355                 360                 365

Tyr Arg Arg His Asn Ile Arg Thr Phe Ser Ala Gly Gly Val Phe Glu
        370                 375                 380

Gln Asp Asp Gly Glu Asn Trp Val Glu Ile Gln Lys Gly Leu Arg Gly
385                 390                 395                 400

Tyr Lys Ala Lys Ser Gln Pro Leu Asn Ala Gln Met Gly Leu Gly Arg
                    405                 410                 415

Ser Gln Thr Gly His Pro Asp Phe Pro Gly Asn Val Gly Tyr Val Tyr
                    420                 425                 430

Ala Glu Glu Ala Ala Arg Gly Met Tyr His His Trp Met Arg Met Met
                    435                 440                 445

Ser Glu Pro Ser Trp Ala Thr Leu Lys Pro
        450                 455
```

METHOD FOR PREPARING PTEROCARPAN

This is a National Phase Application filed under 35 U.S.C. 371 as a national stage of PCT/KR2010/005891, filed on Aug. 31, 2010, an application claiming the benefit from Korean Application No. 10-2010-0027000, filed on Mar. 25, 2010, the entire content of each of which is hereby incorporated by reference in its entirety.

TECHNICAL FIELD

The present invention disclosed herein relates to a novel method for preparing pterocarpans.

More particularly, the present invention relates to a novel method for preparing enantiopure pterocarpans.

The Sequence Listing submitted in the test format (.txt) filed on Feb. 1, 2013, named "GWP120058PCTUS Sequence Listing.txt", (created on Jan. 31, 2013, 10 KB), is incorporated herein by reference.

BACKGROUND ART

Aromatic hydrocarbons, which are common environmental pollutants, may be metabolized aerobically through the initial activation of the aromatic ring initiated by the insertion of oxygen atoms by monooxygenase or dioxygenase enzymes from bacteria [9, 24]. Such aerobic biotransformations may result in the production of intermediates that contain epoxide or dihydrodiol functional groups that may be then further metabolized. It is well known that heme-type cytochrome P450 generally produce aromatic epoxides that may be further metabolized to trans-dihydrodiols [3, 25] while non-heme bacterial dioxygenases produce cis-dihydrodiols from aromatic ring structures (FIG. 1) [28, 32].

Recently, the present inventors reported flavanone epoxide formation by the biphenyl dioxygenase (BDO) of *Pseudomonas pseudoalcaligenes* strain KF707 (SEQ ID NO:3) after expression in *Escherichia coli*, and this unique monooxygenase activity was explained based on the structural properties of the flavanone in the active site [10]. In this case, the flavanone B-ring was unable to form the biphenyl-type structure required for dihydrodiol formation due to the position of the C-3 tetrahedral center on the flavanone structure and may be compared to previous studies where flavanone substrates that possessed the same B-ring conformation as biphenyl were biotransformed to flavone cis-dihydrodiol by biphenyl dioxygenase [20, 27].

Flavonoids are a large group of natural products that have recently been garnering much attention in the disciplines of nutrition, food science, environmental science, and pharmacology due to their potential beneficial effects on health [19]. Actually, flavonoids exhibit inhibitory effect on capillary permeability, peripheral circulation improving effect, anti-inflammatory effect, anti-atherogenic effect, antioxidant effect, anti-allergic effect, and anti-cancer effect, and thus have potential uses as medicine [2, 12, 15, 34]. For example, isoflavones, such as genistein (4',5,7-trihydroxyisoflavone) and daidzein (4',7-dihydroxyisoflavone), are natural edible phytoestrogens found mainly in leguminous plants, and due to their structure similar to a mammalian estrogen [13, 17, 35], they appear to play an important role in preventing hormone-dependent diseases such as breast cancer, prostate cancer, and osteoporosis [1, 11, 14, 18].

The study of BDO biotransformation of flavonoids may aid in the production of new biologically active compounds as well as provide mechanistic insights into the functioning of BDO. The present inventors reported the absolute configurations of four isoflavan-4-ol stereoisomers in the previous study [36].

Throughout the entire specification, many papers and patent documents are referenced and their citations are represented. The disclosures of cited papers and patent documents are entirely incorporated by reference into the present specification, and the level of the technical field within which the present invention falls and details of the present invention are explained more clearly.

DISCLOSURE

Technical Problem

The present inventors have studied and tried to develop novel methods for synthesizing flavonoids that have recently been garnering much attention in the disciplines of nutrition, food science, environmental science, and pharmacology, and consequently, accomplished to synthesize enantiopure pterocarpan from isoflavan-4-ol, thereby completing the present invention.

Therefore, the present invention is to provide a novel method for preparing pterocarpan.

Other purposes and benefits of the present invention become clear by the following detailed description of invention, claims, and drawings.

Technical Solution

In accordance with an exemplary embodiment of the present invention, a method for preparing pterocarpans includes the steps of: (a) contacting a substrate, isoflavan-4-ol, and an enzyme, biphenyl dioxygenase, to form isoflavan-4-ol-2,3-epoxide; and (b) forming pterocarpan from isoflavan-4-ol-2,3-epoxide.

The present inventors have studied and tried to develop novel methods for synthesizing flavonoids that have recently been garnering much attention in the disciplines of nutrition, food science, environmental science, and pharmacology, and consequently, accomplished to synthesize enantiopure pterocarpans from isoflavan-4-ols, thereby completing the present invention.

Isoflavan-4-ols used in the present invention are represented by the following chemical formula 1, and exist in four stereoisomers: (3S,4S)-cis-isoflavan-4-ol, (3R-4R)-cis-isoflavan-4-ol, (3R,4S)-trans-isoflavan-4-ol, and (3S,4R)-trans-isoflavan-4-ol.

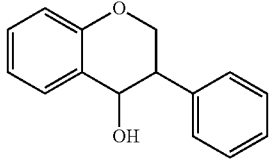

Chemical formula 1

In one embodiment, isoflavan-4-ol is synthesized from the reduction of isoflavones in the presence of Pd/C and ammonium formate under nitrogen atmosphere as described in the document [36].

In the preferred embodiment, isoflavan-4-ol is transformed by biphenyl dioxygenase into an intermediate product, isoflavan-4-ol-2,3-epoxide. Biphenyl dioxygenase is regiospecific for four isoflavan-4-ol stereoisomers, and exhibits a stereospecific unique monooxygenase activity to form the corresponding epoxides.

The corresponding epoxides may be represented by chemical formula 2, and exist in four stereoisomers: (3S,4S)-cis-isoflavan-4-ol-2,3-epoxide, (3R-4R)-cis-isoflavan-4-ol-2,3-epoxide, (3R,4S)-trans-isoflavan-4-ol-2,3-epoxide, and (3S,4R)-trans-isoflavan-4-ol-2,3-epoxide.

Chemical formula 2

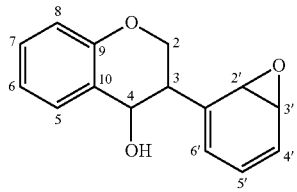

When isoflavan-4-ol is transformed into isoflavan-4-ol-2,3-epoxide by using biphenyl dioxygenase in the present invention, the absolute configuration of C3 and C4 on the B-ring of isoflavan-4-ol is identically maintained also in the intermediate product, isoflavan-4-ol-2,3-epoxide. For example, when enantiopure (3S,4S)-cis-isoflavan-4-ol is used as the substrate, enantiopure (3S,4S)-cis-isoflavan-4-ol-epoxide is formed as the intermediate product.

In one embodiment, the step (a), that is, transforming isoflavan-4-ol into isoflavan-4-ol-2,3-epoxide, is carried out, by adding purified enzyme biphenyl dioxygenase to the substrate isoflavan-4-ol to yield isoflavan-4-ol-2,3-epoxide or by using bacterial cells expressing biphenyl dioxygenase to yield isoflavan-4-ol-2,3-epoxide in large quantities.

The bacteria may include *Lactobacillus, Bifidobacterium, Escherichia coli, Aquificae, Bacteroids, Chlamydia, Spirochaete*, and the like, and preferably be, but not limited to, *Escherichia coli*.

Biphenyl dioxygenase may be one purchased commercially to use, and biphenyl dioxygenase derived from any organisms may be used, but biphenyl dioxygenase derived from *Pseudomonas pseudoalcaligenes* or *Rhodococcus* species is preferable to use. Most preferably, biphenyl dioxygenase of amino acid sequence of SEQ ID NO:2 or SEQ ID NO:3 is used.

In one embodiment of the present invention where biphenyl dioxygenase derived from *Pseudomonas pseudoalcaligenes* was used, the relative reactivity of the stereoisomers was in the following order: (3S,4S)-cis-isoflavan-4-ol>(3R,4S)-trans-isoflavan-4-ol>(3S,4R)-trans-isoflavan-4-ol>(3R,4R)-cis-isoflavan-4-ol.

The present inventors found that isoflavan-4-ol-2,3-epoxide formed as above is naturally transformed into pterocarpan. This transformation which occurs in step (b) in the present invention is presumed to be caused by structural instability of isoflavan-4-ol-2,3-epoxide.

Pterocarpans, the structural backbones found in plant-protective phytoalexins, such as maackiain from *Cicer arietinum* and medicarpin from *Medicago sativa*, are represented by the following chemical formula 3 and exist in four stereoisomers: (3S,4S)-cis-pterocarpan, (3R,4R)-cis-pterocarpan, (3S,4R)-trans-pterocarpan and (3R,4S)-trans-pterocarpan.

Chemical formula 3

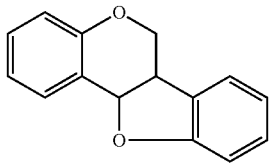

In step (b) of the present invention, the absolute configuration of C3 and C4 on the B-ring is unchanged and identically maintained. For example, enantiopure (3S,4S)-cis-isoflavan-4-ol-2,3-epoxide is transformed into enantiopure (3S,4S)-cis-pterocarpan.

In conclusion, if, for example, enantiopure (3S,4S)-cis-isoflavan-4-ol is used as the substrate, it goes through enantiopure (3S,4S)-cis-isoflavan-4-ol-epoxide, the intermediate product, and enantiopure (3S,4S)-cis-pterocarpan is obtained. Thus, the present invention provides the novel method for preparing enantiopure pterocarpans.

Advantageous Effects

The gist of characteristic and benefit of the present invention is as follows:

(i) The present invention provides a novel method for preparing pterocarpan from isoflavan-4-ol.

(ii) With the use of the method of the present invention, the absolute configuration of C3 and C4 on the B-ring of isoflavan-4-ols is maintained identically also in pterocarpans, and thus, enantiopure pterocarpans can be efficiently prepared.

BEST MODE

Figure 1:
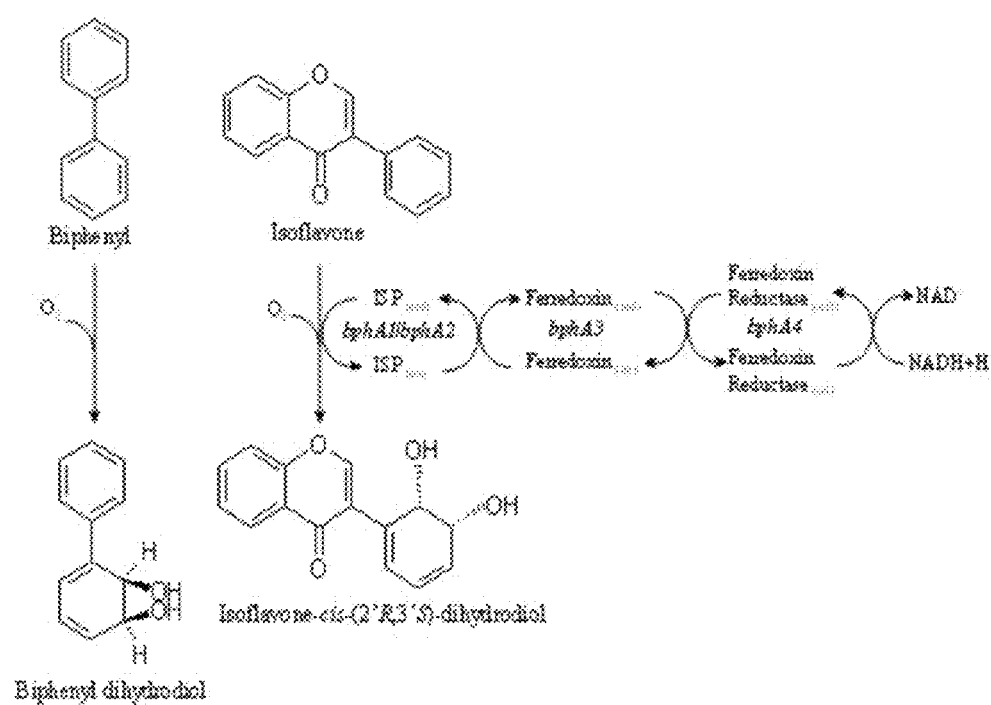
FIG. 1 shows reactions of biphenyl dioxygenase of *P. pseudoalcaligenes* strain KF707 (SEQ ID NO:3) with the physiological substrate biphenyl and non-physiological substrate isoflavone.

Hereinafter, the present invention will be described in detail through embodiments. These embodiments are just for exemplifying the present invention, and it is apparent to those skilled in the art that the scope of the present invention is not limited by these embodiments.

Embodiments

Materials and Methods

1. Chemicals

Isoflavone was purchased from Indofine Chemical Company (Hillsborough, N.J., USA). Acetonitrile, ethyl acetate, and methanol (HPLC grade) were purchased from Fischer (Pittsburgh, Pa., USA). The four isoflavan-4-ol stereoisomers, (3S,4S)- and (3R,4R)-cis-isoflavan-4-ols, and (3S,4R)- and (3R,4S)-trans-isoflavan-4-ols, were synthesized and purified as described in the document [36].

2. Bacterial Strain and Culture Conditions

*Escherichia coli* JM109 (pJHF108) which carries the dioxygenase gene derived from *P. pseudoalcaligenes* strain KF707 were provided by K. Furukawa, Kyushu University, Japan. Cloning of *E. coli* JM109 (pJHF108) can be easily done by those skilled in the art according to the paper (Hirose, J., A. Suyama, T. Zaiki, S. Hayashida, and K. Furukawa, Construction of hybrid biphenyl (bph) and toluene (tod) genes for functional analysis of aromatic ring dioxygenases, Gene, 138:27-33 (1994)). Sequence of dioxygenase derived from *P. pseudoalcaligenes* strain KF707 in the present embodiment is a nucleotide sequence of SEQ ID NO:1.

*E. coli* JM109 (pJHF108) was seed cultivated in 50 mL of LB medium containing ampicillin 50 mg/mL at 37° C. for 12 hours. The cultivated seed was inoculated to a 5-L fermentor (BioFlo 3000, Korea fermentor Co., Korea) containing 4.5 L of LB medium and 50 mg/mL of ampicillin, and mixed at 37° C. at 200 rpm for 8 hours. The culture broth was centrifuged at 8,000 g for 10 minutes using VS-21SMT centrifuge (Vision Scientific Co., Bucheon, Korea). Cells were washed three times with 100 mM minimal salt buffer and resuspended in the same buffer, adjusting to the optical density at 600 nm using a UV/visible spectrophotometer (Shimadzu, UV-1601PC, Kyoto, Japan).

3. Biotransformation Reactions and Metabolite Extraction

Stock solutions (100 mM) of each purified isoflavan-4-ol stereoisomer, (3S,4S)- and (3R,4R)-cis-isoflavan-4-ols and (3S,4R)- and (3R,4S)-trans-isoflavan-4-ols were prepared in a mixture of dimethyl sulfoxide and methanol (2:1, v/v) and added to the resuspended cells at a final concentration of 100 µM. Glucose was added as a reaction energy source at a final concentration of 100 µM. The reaction mixture was incubated on a rotary shaker at 200 rpm at 37° C. for 18 hours, and then extracted with three volumes of ethyl acetate. The ethyl acetate extract was evaporated to dryness with a rotary evaporator (Eyela, Tokyo, Japan) in vacuo, and the residue was dissolved in methanol and filtered through a 0.2 µm Whatman PVDF syringe filter prior to LC-MR analysis.

4. High-Performance Liquid Chromatography

Analytical HPLC was carried out using a Varian Prostar HPLC apparatus (Walnut Creek, Calif.) equipped with a photodiode array (FDA) detector. For the analysis of isoflavan-4-ol stereoisomers and their metabolites, a Waters Spherisorb ODS-2 column (5 mm particle size, 4.6 mm×25 cm, Milford, Mass.) was used. The mobile phase was operated as a linear gradient that made up of water-acetonitrile containing 0.1% formic acid (10% acetonitrile at 0 min, 40% acetonitrile at 15 min, 90% acetonitrile at 25 min, and 90% acetonitrile at 40 min). The flow rate was 1 mL/min and UV detection was performed at 270 nm. For the analysis of enantiomers of cis- and trans-isoflavan-4-ol, a Sumi Chiral OA-7000 column (5 mm, 4.6 mm×25 cm, Sumika Chemical Analysis Service, Ltd., Osaka, Japan) and mobile phase composed of 60:40 (v/v) of 20 mM phosphate buffer (pH 3.0) and acetonitrile were used. The flow rate was 1 mL/min and UV detection was performed at 270 nm.

5. Liquid Chromatography/Mass Spectrometry

Liquid chromatography/mass spectrometry (LC-MS) was performed by coupling an Alliance 2695 (Waters Corporation, Milford, Mass.) LC (SunFire C18 column; 3.5 mm, 2.1×150 mm, Waters) to a Quattro LC triple quadrupole tandem mass spectrometer (Waters, Milford, Mass.) in positive electrospray ionization (ESI+) mode. For LC analysis, the mobile phase, elution program, and detection were the same as those of analytical HPLC and the flow rate was 0.2 mL/min. For MS analysis, the source temperature, desolvation temperature, electron multiplier voltage, and capillary voltage were kept at 150° C., 350° C., 700 V, and 3.0 kV, respectively. The cone voltage was 25 V. The cone gas and desolvation gas were ultra-pure nitrogen set at 30 l/h and 500 l/h, respectively.

6. Liquid Chromatography/Nuclear Magnetic Resonance Spectroscopy

LC-NMR analyses were performed under ambient conditions using a Prostar 230 ternary gradient pump, a Prostar 430 autosampler (Varian, Walnut Creek, Calif., USA), and a Prostar 335 photodiode array detector (Varian, Mulgrave, Victoria, Australia). Separation was carried out using a Hydrosphere-C18 column (3 µm particle size, 150×4.6 mm, YMC, Kyoto, Japan) and the mobile phase made up of acetonitrile and deuterated water (D2O). The gradient program was as follows: 25% acetonitrile at 0 min and 60% acetonitrile at 35 min. The flow rate was maintained at 0.4 mL/min. The chromatographic profile was recorded at 270 nm.

NMR data were acquired using a Varian NMR system 500 MHz (Varian, Palo Alto, Calif. JSA) equipped with cold probe with a 60 µL flow cell. $^1$H-NMR spectra were obtained in stop-flow mode. Varian WET solvent suppression was used to suppress the acetonitrile and the residual water peaks. COSY spectra were obtained using water suppression enhancement through TI effect gradient correlation spectroscopy (WETgCOSY) pulse sequencing in which the WET element was incorporated into the gCOSY sequence.

7. Biotransformation Kinetics of Purified (3S,4S)- and (3R,4R)-cis-isoflavan-4-ols and (3S,4R)- and (3R,4S)-trans-isoflavan-4-ols Biotransformation kinetics by whole cells of *E. coli* expressing biphenyl dioxygenase was performed as follows. The bacterial culture was prepared as described above, resuspended in 50 mL of phosphate buffer containing 1 mM glucose in a 250 mL flask, and adjusted to a final culture concentration of OD 600 nm=0.6. Then, the bacterial culture was incubated with 250 μM each of four purified isoflavan-4-ol stereoisomers ((3S,4S)- and (3R,4R)-cis-isoflavan-4-ols and (3S,4R)- and (3R,4S)-trans-isoflavan-4-ols) on a rotary shaker (200 rpm) at 37° C. The bacterial cultures (2 mL) were extracted with ethyl acetate, and the solvent was evaporated to dryness as described above. Quantification of metabolites and parent compound by using HPLC with time was monitored in triplicate experiments. Due to the instability of metabolites which were produced from parent compound, the quantity was calculated from the peak area as compared to the standard curve of the parent compound.

8. Enzyme-Substrate Docking Study

Because the only reported X-ray protein crystallographic structure of BDO is from a *Rhodococcus* species, the present inventors changed the amino acid residues in the substrate binding site and substrate channel of *Rhodococcus* sp. strain RHA1 BDO (SEQ ID NO:2) to those of KF707 BDO (SEQ ID NO:3). The source of the X-ray protein structure (pdb code=1ULJ) was obtained from the RCSB Protein Data Bank (http://www.pdb.org), and the corresponding amino acid residues were mutated using Swiss-PDB Viewer software. The Chimera Program was used for the enzyme-substrate docking study, including substrate volume calculation.

Results and Discussion

Figure 2:
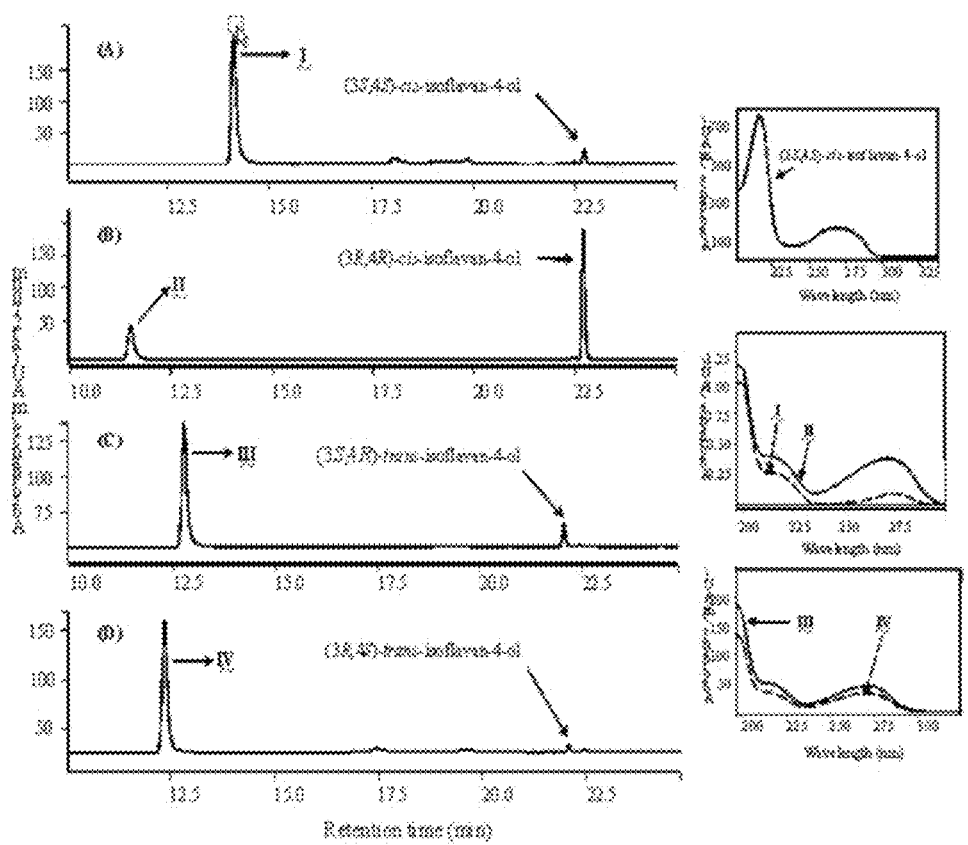
FIG. 2 shows HPLC elution profile of (3S,4S)-cis-isoflavan-4-ol (A), (3R,4R)-cis-isoflavan-4-ol (B), (3S,4S)-trans-isoflavan-4-ol (C) and (3R,4S)-trans-isoflavan-4-ol (D) reaction metabolites produced by whole cells of *E. coli* expressing the biphenyl dioxygenase of *P. pseudoalcaligenes* strain KF707 (SEQ ID NO:3). Inserted drawings show UV-visible spectra of (3S,4S)-cis-isoflavan-4-ol and metabolites I, II, III, and IV.

Purified (3S,4S)- and (3R,4R)-cis-isoflavan-4-ols and (3S,4R)- and (3R,4S)-trans-isoflavan-4-ols were used as substrates for *E. coli*-expressed biphenyl dioxygenase derived from *P. pseudoalcaligenes* strain KF707 (SEQ ID NO:3). Metabolites produced from (3S,4S)- and (3R,4R)-cis-isoflavan-4-ols and (3S,4R)- and (3R,4S)-trans-isoflavan-4-ols, were designated as I, II, III, and IV, respectively (FIG. 2). Metabolites I, II, III, and IV were eluted at 14.6, 11.8, 12.9, and 12.4 min each, and had identical UV absorption peaks at 219 and 275 nm (FIG. 2). Therefore, it was concluded that all four metabolites were expected to have the same valence electron energies, meaning that they included the same or closely related molecular structures and functional groups.

Figure 3A:
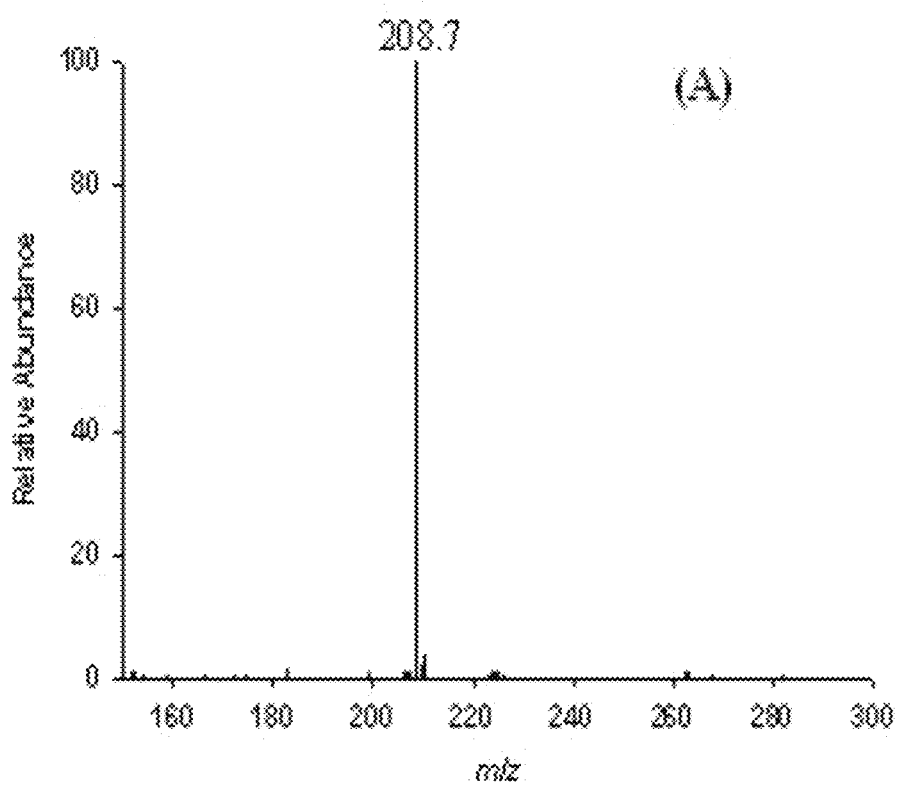
FIG. 3 is ESI-MS spectra of cis-isoflavan-4-ol (A), its metabolite I (B), and abiotic product (C).
Figure 3B:
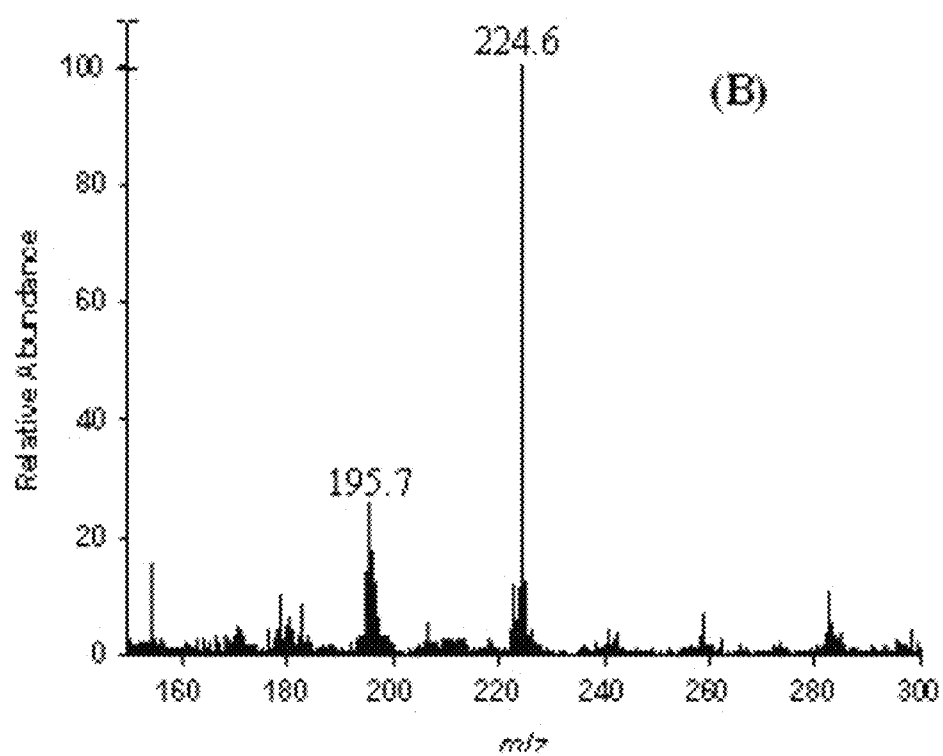
Figure 3C:
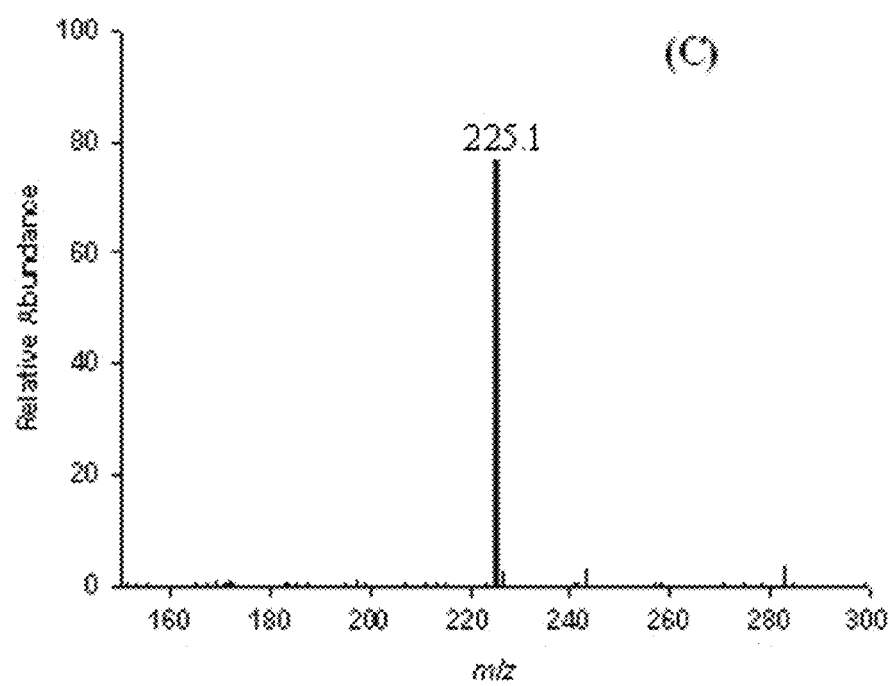
Figure 7:
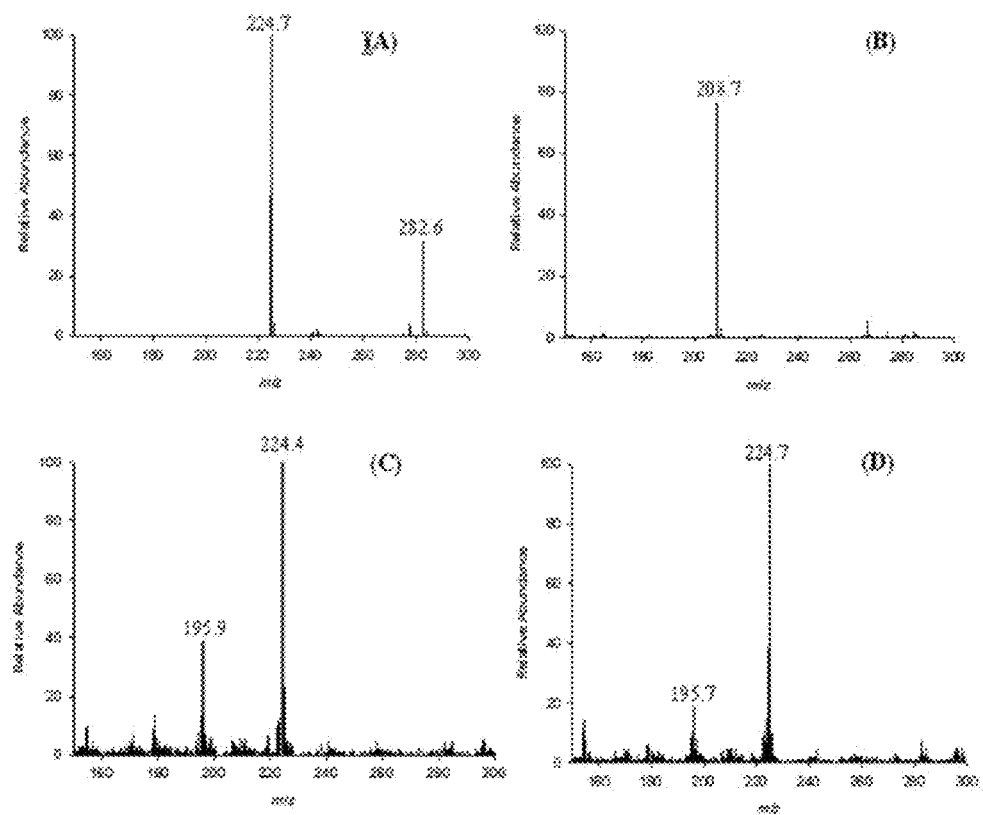
FIG. 7(A) is an ESI-MS spectrum of metabolite II derived from cis-isoflavan-4-ol.
FIG. 7(B) is a spectrum of trans-isoflavan-4-ol.
FIG. 7(C) is a spectrum of metabolite III of trans-isoflavan-4-ol.
FIG. 7(D) is a spectrum of metabolite IV of trans-isoflavan-4-ol.

LC-MS analyses indicated that the isoflavan-4-ols showed a peak at m/z 208.7 corresponding to [M−(H2O)]+ (FIG. 3A and FIG. 7) and metabolites I, II, III, and IV showed peaks at m/z 224.6, 224.7, 224.4, and 224.7, respectively, presumably corresponding to [M−(H2O)]+ species (FIG. 3B and FIG. 7). The 16 mass unit differences that were consistently observed between the substrates and metabolites indicated that epoxidation or monohydroxylation occurred, and it was concluded that the isoflavan-4-ol metabolites were derivatives of isoflavan-4-ol compounds that possessed either a phenol or an epoxide functional group.

The present inventors performed LC-NMR (500 MHz, D2O/acetonitrile) experiment to identify structures of metabolites I, II, III, and IV, and the resulting 1H NMR spectra were shown in the following Table 1.

TABLE 1

| δ of $^1$H | | | | | $^1$H-$^1$H | |
|---|---|---|---|---|---|---|
| I | II | III | III-a | IV | COSY | Assignment |
| 4.21(dd, 10.8, 3.5) | 4.20(dd, 10.8, 3.6) | 4.29(dd, 10.8, 2.5) | ~4.31(water overlapped) | 4.21(dd, 11.0, 3.1) | 2b, 3 | 2a |
| 4.17(t, 10.8) | 4.14(t, 10.8) | 4.2(m) | ~4.31(water overlapped) | 4.1(m) | 2a, 3 | 2b |
| 2.80(dr, 10.8, 3.5) | 2.86(dt, 10.8, 3.4) | 2.67(m) | 3.42(dt, 5.9, 4.0) | 2.67(m) | 2a, 2b, 4 | 3 |
| 4.75(d, 3.4) | 4.79(d, 3.4) | 4.71(5.8) | 4.90(d, 5.9) | 4.78(d, 6.2) | 3 | 4 |
| 7.25(d, 7.8) | 7.26(d, 7.9) | 7.29(d, 7.8) | 7.32(d, 7.5) | 7.34(d, 7.5) | 6 | 5 |
| 6.9(t, 7.8) | 6.9(t, 7.8) | 6.9(d, 7.5) | 6.9(t, 7.7) | 6.93(t, 7.5) | 5, 7 | 6 |
| 7.18(t, 7.6) | 7.18(t, 8.1) | 7.16(d, 7.8) | 7.15(t, 7.7) | 7.16(t, 7.8) | 6, 8 | 7 |
| 6.79(d, 8.0) | 6.78(d, 8.0) | 6.75(d, 7.9) | 6.75(d, 7.8) | 6.73(d, 7.8) | 7 | 8 |
| 4.02(ethylacetate overlapped) | 3.99(d, 5.69) | 3.94(d, 5.4) | ~ | 3.97(d, 5.78) | 3' | 2' |
| 4.3(m) | 4.32(m) | 4.20(m) | 6.79(d, 7.9) | 4.28(m) | 2', 4' | 3' |
| 5.7(dd, 9.5, 3.0) | 5.68(dd, 9.5, 2.7) | 5.65(dd, 9.2, 2.2) | 7.04(t, 7.8) | 5.65(dd, 9.7, 2.0) | 3', 5' | 4' |
| 5.90(m) | 5.89(m) | 5.82(m) | 6.70(t, 7.6) | 5.78(m) | 4', 6' | 5' |
| 5.65(d, 5.5) | 5.74(d, 5.5) | 5.85(d, 5.3) | 6.98(d, 7.6) | 5.57(d, 5.4) | 5' | 6' |

Figure 8:
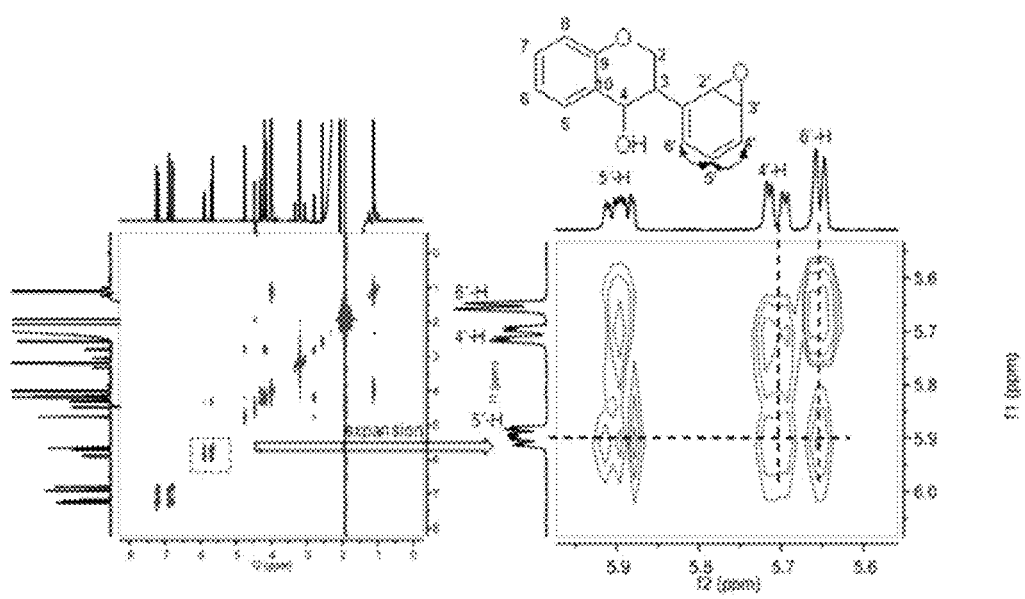
FIG. 8 is a WETgCOSY spectrum of metabolite III of (3S,4R)-trans-isoflavan-4-ol.

As shown in Table 1, the 1H NMR spectra of metabolites I, II, III, and IV exhibited similar patterns. Four aromatic peaks at δ 6.7~7.3 were assigned to A-ring protons in isoflavan-4-ols. Three olefinic peaks at δ 5.5~5.9 and two oxygenated aliphatic protons at δ 4.0~4.3 were detected, which suggested epoxide formation on the B-ring. According to the WETgCOSY spectra obtained from metabolite III of (3S,4R)-trans-isoflavan-4-ol (FIG. 8), the presence of three olefinic protons confirmed the epoxide formation between C2' and C3' on the B-ring of the corresponding isoflavan-4-ols [10]. These LC-NMR data were in agreement with LC-MS data, which showed the addition of an oxygen atom (m/z 208→224) in metabolites I, II, III, and IV.

The observed coupling constants of Metabolites I and II (JH3,4=3.4 Hz) indicated that the H—C3-C4-H dihedral angle was close to 50°, which suggested that metabolites I and II may be characterized by cis-isoflavan-4-ol. In metabolites III and IV, JH3,4 values were observed at 5.8 and 6.2 Hz, respectively, which indicated that metabolites III and IV were trans-isoflavan-4-ol [36]. From these results, it was concluded that the configurations of the C3 and C4 centers on the B-ring of the isoflavan-4-ol stereoisomers did not change during the BDO reaction.

From LC-NMR analyses, the epoxidation of isoflavan-4-ol by BDO was confirmed to be a regiospecific and stereospecific reaction. If the oxygen atom transfer reaction occurred on a different double bond or on a different side of the B-ring, more than one metabolite peak would have been observed from the chromatogram due to the formation of regio- or diastereomeric isomers.

The following Table 2 shows production amounts of epoxides from isoflavan-4-ols by *P. pseudoalcaligenes* KF707 BDO (SEQ ID NO:3).

TABLE 2

| Substrates[a] | | | Corresponding epoxides (µM)[b] produced after 5 h reaction |
|---|---|---|---|
| Cis-isoflavan-4-ol | (3S,4S) | I | 194.8 ± 5.5 |
| | (3R,3R) | II | 40 ± 4.0 |
| Trans-isoflavan-4-ol | (3S,4R) | III | 141.1 ± 6.2 |
| | (3R,4S) | IV | 163.3 ± 6.8 |

[a]Initial concentration of substrates: 250 µM
[b]Values are means of triplicate experiments ± standard errors From Table 2, the substrate preference of BDO between cis-enantiomers was observed in which epoxide production from (3S,4S)-cis-isoflavan-4-ol was about 4.8-fold higher than that from (3R,4R)-cis-isoflavan-4-ol after 5 h of reaction. However, such preference of BDO was not observed distinctively between two trans-enantiomers. The substrates (3S,4R)- and (3R,4S)-trans-isoflavan-4-ols were biotransformed to 141.1 and 163.3 µM of the corresponding epoxides, respectively, during the 5-h reaction. Therefore, it appears that the BDO of *P. pseudoalcaligenes* KF707 (SEQ ID NO:3) has different substrate preferences for the four stereoisomers of the isoflavan-4-ols in a regiospecific and stereospecific manner.

Figure 9:
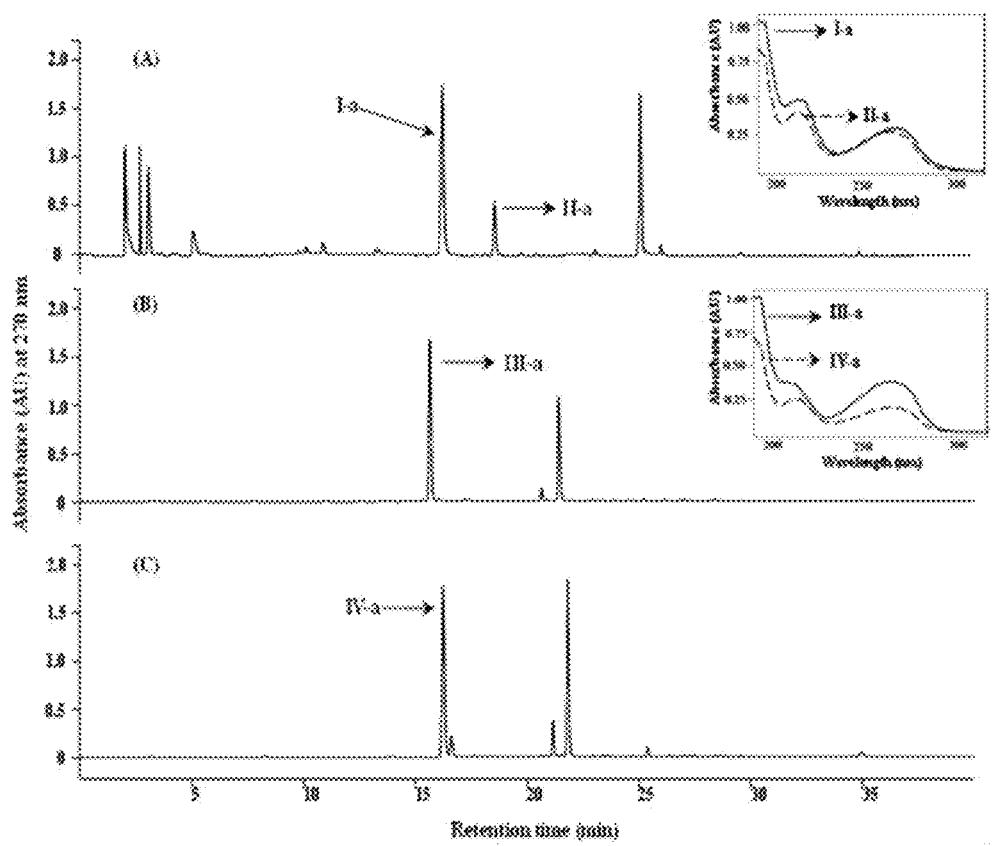
FIG. 9(A) is an HPLC elution profile of abiotic products I-a and II-a derived from cis-isoflavan-4-ol-2',3'-epoxide.
FIG. 9(B) is a profile of III-a derived from (3S,4R)-trans-isoflavan-4-ol-2',3'-epoxide.
FIG. 9(C) is an elution profile of IV-a derived from (3R,4S)-trans-isoflavan-4-ol-2',3'-epoxide. Inserted drawings are UV-visible spectra of the above abiotic products.
Figure 10A:
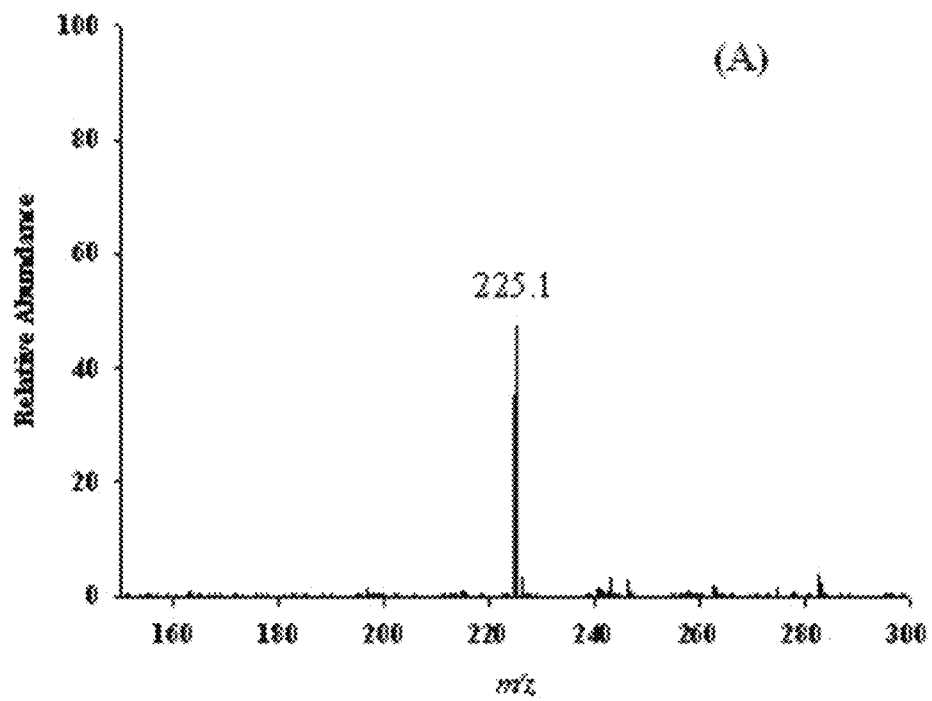
FIG. 10 is ESI-MS spectra of abiotic products II-a derived from (3R,4R)-cis-isoflavan-4-ol-2',3'-epoxide (A), III-a derived from (3S,4R)-trans-isoflavan-4-ol-2',3'-epoxide (B), and IV-a derived from (3R,4S)-trans-isoflavan-4-ol-2',3'-epoxide.
Figure 10B:
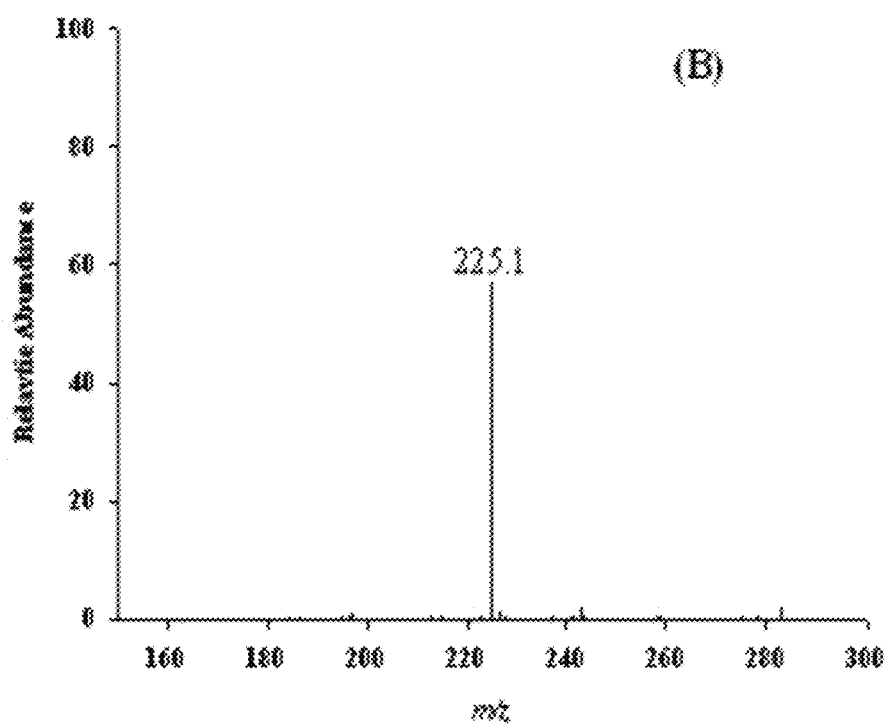
Figure 10C:
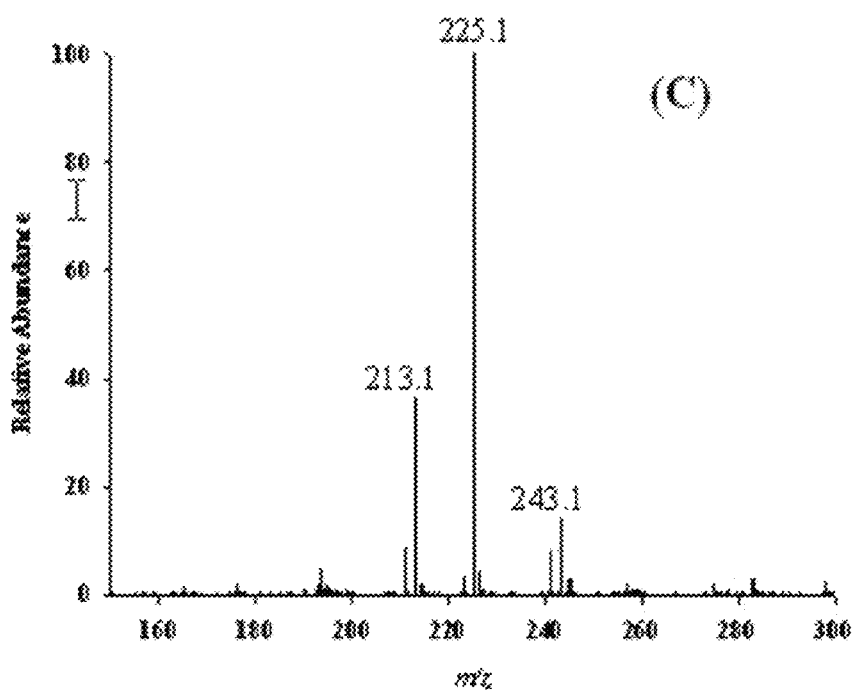

Interestingly, the epoxide metabolites produced from the isoflavan-4-ols were unstable and were rearranged to energetically favorable chemical structures during reaction and analyses. All four isoflavan-4-ol-2',3'-epoxides were transformed to abiotic compounds (I-a, II-a, III-a, IV-a from I, II, III, and IV, respectively) with different HPLC retention times compared to those of the epoxide metabolites (FIG. 9).

HPLC results for four abiotic compounds I-a, II-a, III-a, and IV-a were shown in the following Table 3.

TABLE 3

| | Data for abiotic products produced from each epoxide | |
|---|---|---|
| Metabolites | HPLC retention time (min) | Absorption maximum (nm)[a] |
| (3S,4S)-cis-isoflavan-4-ol-2',3'-epoxide | 16.1 | 272 |
| (3R,4R)-cis-isoflavan-4-ol-2',3'-epoxide | 17.2 | 270 |
| (3S,4R)-trans-isoflavan-4-ol-2',3'-epoxide | 15.6 | 270 |
| (3R,4S)-trans-isoflavan-4-ol-2',3'-epoxide | 16.2 | 271 | b Values were obtained using HPLC equipped with a photodiode array detector.

Figure 11A:
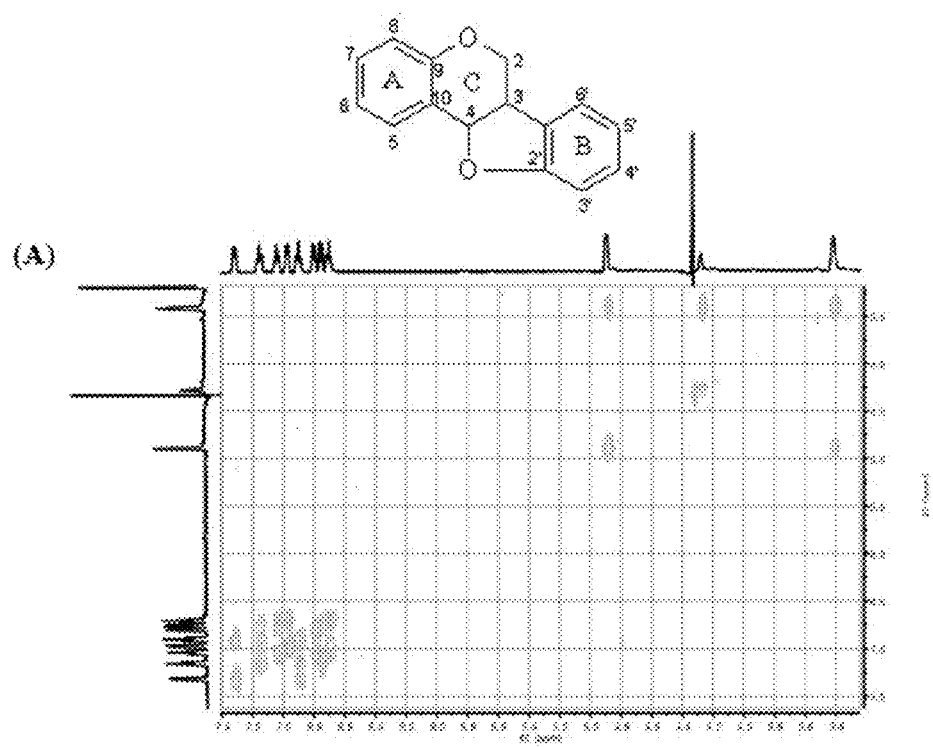
FIG. 11 is WETgCOSY spectra of abiotic product III-a (A), and its aromatic region (B).
Figure 11B:
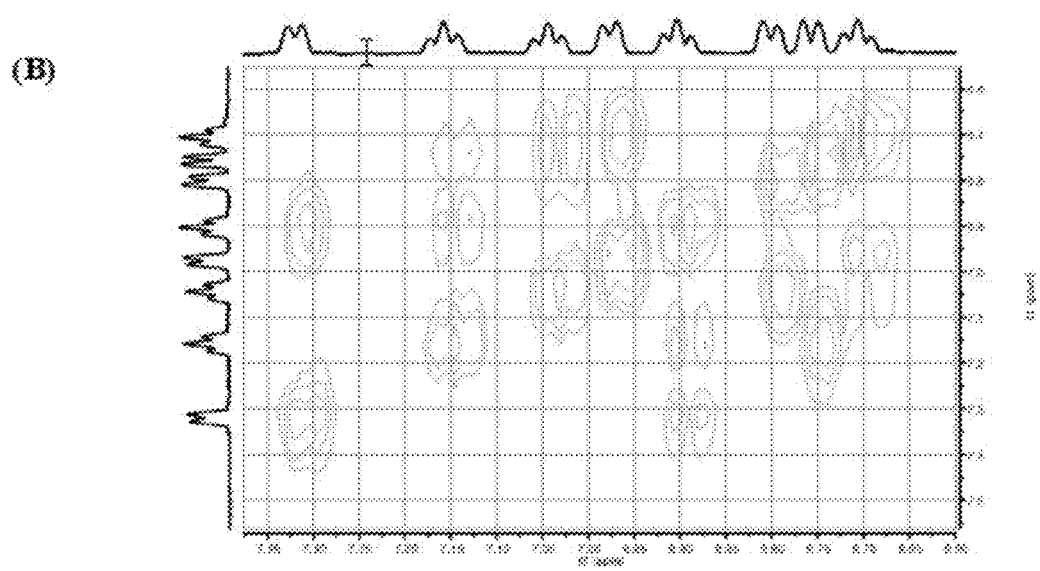

From the above Table 3, four abiotic compounds, I-a, II-a, III-a, and IV-a, were eluted at 16.1, 17.2, 15.6, and 16.2 min, respectively. LC-MS analyses in positive ion mode showed molecular ion peaks [M+H]+ at 225.1 m/z for all abiotic compounds. The result of LC-NMR analysis for III-a among four abiotic compounds showed four aromatic protons (two doublets and two triplets) at δ 6.7~7.3 (Table 1) when compared to epoxide metabolite III and these aromatic protons corresponded to protons of the B-ring of pterocarpan. According to the coupling constants and WETgCOSY (FIG. 11), four protons of the B-ring were adjacent to each other. These NMR results together with LC-MS data, which indicated the subtraction of one oxygen and two hydrogen atoms, enabled the present inventors to identify the formation of an ether linkage between C4 and C2' to form furan.

Figure 4:
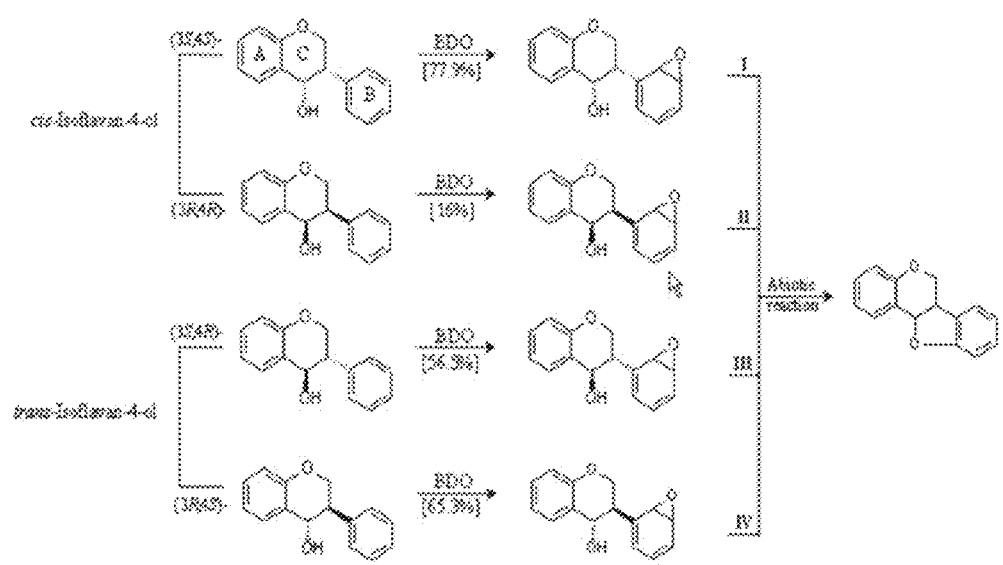
FIG. 4 shows a biotransformation pathway of cis-isoflavan-4-ol and trans-isoflavan-4-ol by biphenyl dioxygenase of *P. Pseudoalcaligenes* KF707 (SEQ ID NO:3). The percentage of each epoxide product is shown in brackets.

Based on the spectroscopic characterizations of the abiotic compounds, the products were identified as pterocarpan diastereomers possessing a 6a,11a-dihydro-6H-benzofuro[3,2-c] benzopyran skeleton. These results suggest that epoxides produced from isoflavan-4-ols by strain KF707 BDO (SEQ ID NO:3) may trigger an abiotic reaction due to their instability (FIG. 4). The formation of pterocarpan products may be explained through bond formation between C4-O and C2' combined with the loss of one molecule of H2O and the detailed mechanism is currently under study. Many pterocarpan derivatives, such as maackiain from *Cicer arietinum* and medicarpin from *Medicago sativa*, are plant-protective phytoalexins produced in response to fungal, bacterial, and viral infections [5]. Some pterocarpans have been known to exhibit not only the above phytoalexins activity, but also anti-tubercular and estrogenic activities [26] and inhibitory activities against HIV-1 in cell cultures [6,7] and to act as antagonists against some snake venoms [23]. Because of the diverse utilities of pterocarpan derivatives, various chemical synthesis methods for pterocarpan have been introduced [21, 22, 33], and the present inventors propose that the BDO-mediated synthesis of pterocarpan may provide another novel route for the production of enantiopure four different type of pterocarpans.

Figure 5:
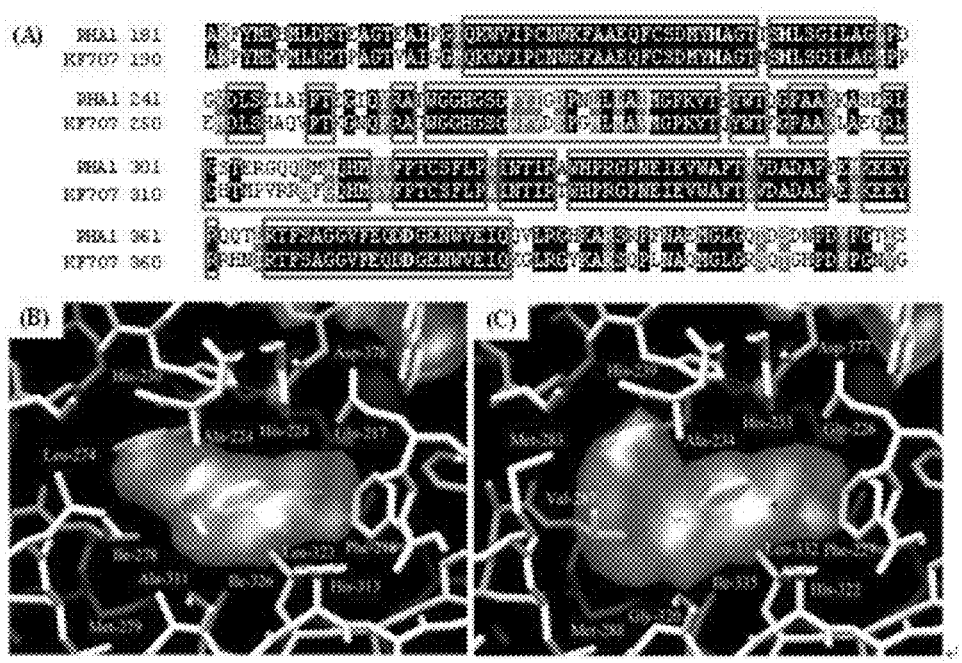
FIG. 5 shows an amino acid sequence alignment of the α-subunits of RHA1 (SEQ ID NO:2) and KF707 (SEQ ID NO:3) BDOs. (A): conserved sequences are marked with a blue box and the residues near the substrate binding site and possible substrate channel are marked with a yellow box. The Fe binding residues are shown with a bold box. Volumes of the substrate binding sites were calculated as 38.33 3 for *Rhodococcus* species (B) and 102.8 3 for *P. pseudoalcaligenes* strain KF707 (C).
Figure 6A:
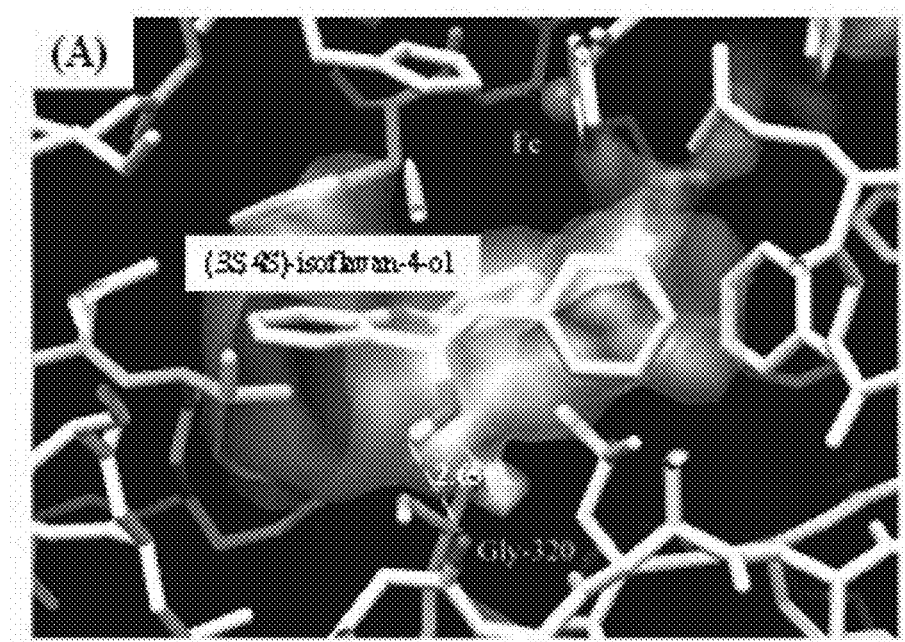
FIG. 6 shows docking model of (3S,4S)-isoflavan-4-ol (A) and (3R,4R)-isoflavan-4-ol (B) in the active site of BDO KF707 (SEQ ID NO:3). The B-ring of the substrate is positioned away from the Fe center. (c) shows the overlapped structures of four isoflavan-4-ol stereoisomers.
Figure 6B:
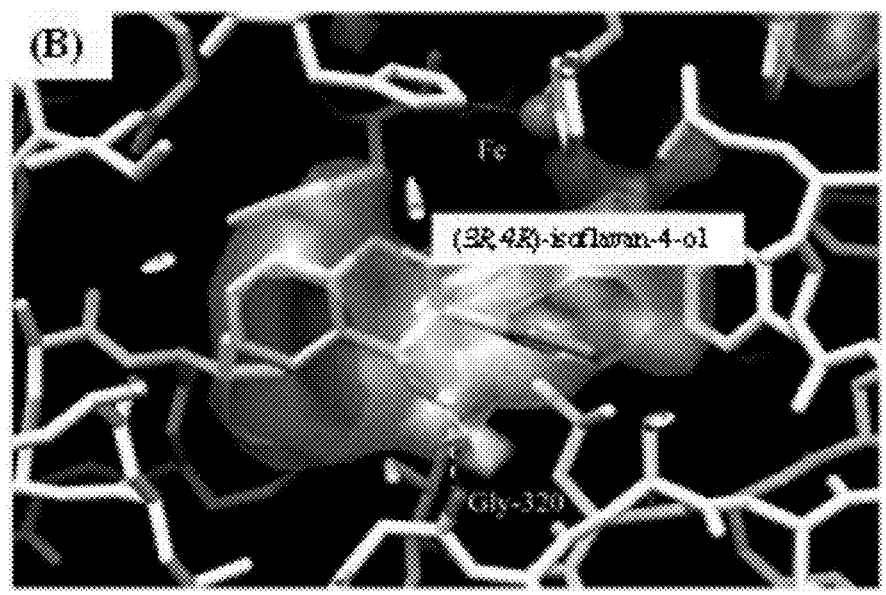
Figure 6C:
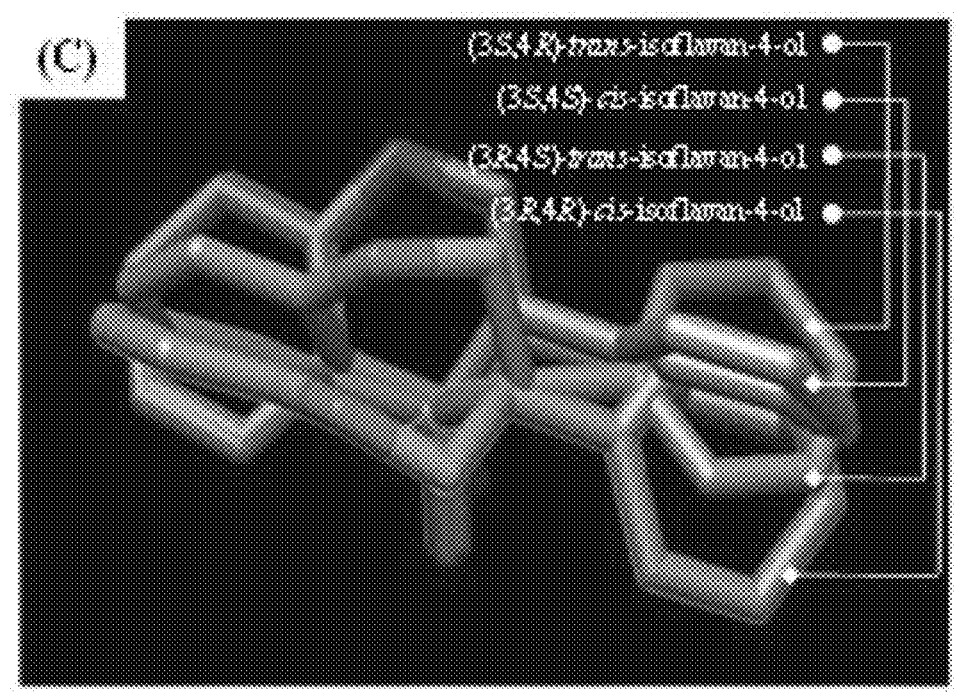

To obtain more insight with regard to the unique activity of BDO toward isoflavan-4-ol stereoisomers, an enzyme-substrate docking study was performed. Since only one X-ray protein crystallographic structure of BDO is available from a Gram-positive PCB-degrading organism, *Rhodococcus* sp. strain RHA1 [8], the amino acid sequences of BDOs from *P. pseudoalcaligenes* strain KF707 (SEQ ID NO:3) were compared to those of BDO from *Rhodococcus* sp. strain RHA1 (SEQ ID NO:2) by aligning important conserved sequences (FIG. 5A). Except for the Fe active site, the two BDOs showed many different amino acid residues inside the substrate binding sites and channel, as well as on the protein surface. In order to compare reaction specificity of enzymes, different amino acid residues between the above two BDOs associated with substrate binding and substrate channel were introduced. The important changes in the amino acid residues in the RHA1 BDO (SEQ ID NO:2) were Leu-274, Ile-278, and Ala-311 in the substrate binding site, which were matched to Met-283, Val-287, and Gly-320, respectively, in the KF707 BDO (SEQ ID NO:3). Accordingly, the reduction of van der Waals surfaces of all three amino acid residues by one methyl group in RHA1 BDO (SEQ ID NO:2) was observed from strain KF707 BDO (SEQ ID NO:3). Therefore, when the volumes of the substrate binding sites between the two proteins were compared, a difference of 102.8 and 38.33 3 were calculated for strain KF707 and strain RHA1, respectively (FIG. 5B and FIG. 5C). Therefore, the BDO of strain KF707 (SEQ ID NO:3) may accommodate a much larger substrate when compared to strain RHA1 (SEQ ID NO:2), and this has been confirmed by other previous reports [8, 16, 27]. Interestingly, the Arg-305 residue in the BDO of strain RHA1 (SEQ ID NO:2), which is thought to be an important residue in the substrate channel, corresponds to the Pro-305 residue in the BDO of strain KF707 (SEQ ID NO:3), and it appears that this difference may alter substrate passage by allowing for a larger substrate to enter the BDO of strain KF707 (SEQ ID NO:3). However, this comparison of volumes of the substrate binding sites between the two proteins cannot fully explain the chlorinated biphenyl degrading mechanism. When compared to strain KF707 [31] which transforms double para-substituted PCB congeners favorably, strain RHA1 has high transformation activity on both ortho- and para-substituted PCB congeners [30]. *Rhodococcus* sp. strain RHA1 transformed even highly-chlorinated PCB congeners, such as heptachlorobiphenyl [29]. After validation of the new BDO structure of strain KF707 (SEQ ID NO:3) as stated above, the isoflavan-4-ol stereoisomers were replaced in the position of biphenyl, and the orientations of the isoflavan-4-ol substrates around the non-heme Fe center were adjusted to allow for epoxide formation on the B-ring. When (3S,4S)-cis-isoflavan-4-ol, which was transformed to the corresponding epoxide in the highest yield among the tested stereoisomers, was docked in the substrate binding site, the substrate fit perfectly in the substrate binding space, and hydrogen bonding formation between the 4-OH of (3S,4S)-cis-isoflavan-4-ol and the α-carbonyl of Gly-320 was observed to occur at a distance of 2.65. On the contrary, the least reactive substrate, (3R,4R)-cis-isoflavan-4-ol, did not fit well in the substrate binding site. When the hydrogen bonding formation between the 4-OH of (3R,4R)-cis-isoflavan-4-ol and the α-carbonyl of Gly-320 was allowed, the reaction moiety of the B-ring was positioned farther from the Fe center (FIG. 6B). It was concluded that the lower reaction rate of (3R,4R)-cis-isoflavan-4-ol was due to the location of the B-ring. For epoxide formation, the B-ring of (3R,4R)-cis-isoflavan-4-ol must go through an energetically unfavorable rotation to be near to the Fe center. To explain the different reactivities of the four stereoisomers of isoflavan-4-ol, four structures were overlapped while the orientations of the 4-OH groups were maintained at the same location in the substrate binding space (FIG. 6C). While the other three stereoisomers were relatively well overlapped with the B-rings toward the Fe reaction center, the structure of (3R,4R)-cis-isoflavan-4-ol was unable to be overlapped with the other three stereoisomers due to the different position of the B-ring compared to the others. In conclusion, the present inventors have reported the biotransformation of four isoflavan-4-ol stereoisomers, (3S,4S)- and (3R,4R)-cis-isoflavan-4-ols, and (3S,4R)- and (3R,4S)-trans-isoflavan-4-ols, to their corresponding epoxides formed between the C2' and C3' positions on the B-ring by biphenyl dioxygenase derived from *P. pseudoalcaligenes* strain KF707 in the present specification. Furthermore, the present inventors have discussed the substrate-specific differences between strains RHA1 (SEQ ID NO:2) and KF707 (SEQ ID NO:3) BDOs and further rationalized the stereoselective absolute configuration-dependent monooxygenase-like epoxide formation of the isoflavan-4-ol stereoisomers by BDO from *P. pseudoalcaligenes* KF707 (SEQ ID NO:3) through the enzyme-substrate docking model study. An understanding of the reaction mechanisms of biphenyl dioxygenase on flavonoids may provide a means for conceiving a useful method for the production of other kinds of enantiopure pterocarpans.

REFERENCES

1. Adlercreutz, H. 2002. Phyto-estrogens and cancer. Lancet Oncol. 3:364-373.
2. Arora, A., M. G. Nair, and G. M. Strasburg. 1998. Antioxidant activities of isoflavones and their biological metabolites in a liposomal system. Arch. Biochem. Biophys. 356: 133-141.
3. Boyd, D. R., and N. D. Sharma. 2002. Enzymatic and chemoenzymatic synthesis of arene trans-dihydrodiols. J. Mol. Catal. B: Enzym. 19-20:31-42.
4. Dewick, M. P., and J. B. Harborne. 1994. The flavonoids, advances in research since 1986. Chapman and Hall, London.
5. Dixon, R. A. 2001. Natural products and plant disease resistance. Nature 411:843-847.
6. Engler, T. A., K. O. LaTessa, R. Iyengar, W. Chai, and K. Agrios. 1996. Stereoselectivity syntheses of substituted pterocarpans with anti-HIV activity, and 5-aza-/5-thia-pterocarpan and 2-aryl-2,3-dihydrobenzofuran analogues. Bioorg. Med. Chem. 4:1755-1769.
7. Engler, T. A., K. O. Lynch Jr., J. P. Reddy, and G. S. Gregory. 1993. Synthetic pterocarpans with anti-HIV activity. Bioorg. Med. Chem. Lett. 3:1229-1232.
8. Furusawa, Y., V. Nagarajan, M. Tanokura, E. Masai, M. Fukud, and T. Senda. 2004. Crystal structure of the terminal oxygenase component of biphenyl dioxygenase derived from *Rhodococcus* sp. strain RHA1. J. Mol. Biol. 342:1041-1052.
9. Gibson, D. T., and R. E. Parales. 2000. Aromatic hydrocarbon dioxygenases in environmental biotechnology. Curr. Opin. Biotechnol. 11:236-243.
10. Han, J., S.-Y. Kim, J. Jung, Y. Lim, J. H. Ahii, S.-I. Kim, and H. G. Hur. 2005. Epoxide formation on the aromatic B ring of flavanone by biphenyl dioxygenase of *Pseudomonas pseudoalcaligenes* KF707. Appl. Environ. Microbiol. 71:5354-5361.
11. Heinonen, S., K. W, and H. Adlercreutz. 1999. Identification of isoflavone metabolites dihydrodaidzein, dihydrogenistein, 6'-OH-dma, and cis-4-OH-equol in human urine by gas chromatography-mass spectroscopy using authentic reference compounds. Anal. Biochem. 274:211-219.
12. Hollman, P. C., and M. B. Katan. 1998. Bioavailability and health effects of dietary flavanols in man. Arch. Toxicol. 20:237-248.
13. Hur, H. G., R. D. Beger, T. M. Heinze, J. O. Lay Jr., J. P. Freeman, and J. D. F. Rafii. 2002. Isolation of an anaerobic intestinal bacterium capable of cleaving the C-ring of the isoflavonoid daidzein. Arch. Microbiol. 178:8-12.
14. Hwang, C. S., H. S. Kwak, H. J. Lim, S. H. Lee, Y. S. Kang, T. B. Choe, H. G. Hur, and K. O. Han. 2006. Isoflavone metabolites and their in vitro dual functions: they can act as an estrogenic agonist or antagonist depending on the estrogen concentration. J. Steroid Biochem. Mol. Biol. 101:246-253.
15. Hwang, E. I., M. Kaneko, Y. Ohnishi, and S. Horinouchi. 2003. Production of plant-specific flavanones by *Escherichia coli* containing an artificial gene cluster. Appl. Environ. Microbiol. 69:2699-2706.
16. Iwasaki, T., H. Takeda, K. Miyauchi, T. Yamada, E. Masai, and M. Fukuda. 2007. Characterization of two biphenyl dioxygenases for biphenyl/PCB degradation in a PCB degrader, *Rhodococcus* sp. strain RHA1. Biosci. Biotechnol. Biochem 71:993-1002.
17. Joannou, G. E., G. E. Kelly, A. Y. Reeder, M. Waring, and C. Nelson. 1995. A urinary profile study of dietary phytoestrogens, the identification and mode of metabolism of new isoflavonoids. J. Steroid Biochem. Mol. Biol. 54:167-184.
18. Kim, M., J. Han, and S.-U. Kim. 2008. Isoflavone daidzein: chemistry and bacterial metabolism. J. Appl. Biol. Chem. 51:253-261.
19. Kim, M., S.-I. Kim, J. Han, X.-L. Wang, D.-G. Song, and S.-U. Kim. 2009. Stereospecific biotransformation of dihydrodaidzein into (3S)-equol by the human intestinal bacterium *Eggerthella* strain Julong 732. Appl. Environ. Microbiol. 75:3062-3068.
20. Kim, S. Y., J. Jung, Y. Lim, J. H. Ahn, S. I. Kim, and H. G. Hur. 2003. Cis-2',3'-dihydrodiol production on flavone B-ring by biphenyl dioxygenase from *Pseudomonas*

*pseudoalcaligenes* KF707 expressed in *Escherichia coli*. Anton. Leeuw. Int. JG 84:261-268.

21. Kiss, L., T. Kurt, S. Antus, and A. B 2003. Chiroptical properties and synthesis of enantiopure cis and trans pterocarpan skeleton. Chirality 15:558-563.
22. Kiss, L., L. Szil, and S. Antus. 2002. A simple conversion of 2'-benzyl oxyflavanone to pterocarpan. Z. Naturforsch., B: Chem. Sci. 57:1165-1168.
23. Nakagawa, M., K. Nakanishi, L. L. Darko, and J. A. Vick. 1982. Structures of cabenegrins A-I and A-II, potent antisnake venoms. Tetrahedron Lett. 23:3855-3858.
24. Nolan, L. C., and K. E. O'Connor. 2008. Dioxygenase- and monooxygenase-catalysed synthesis of cis-dihydrodials, catechols, epoxides and other oxygenated products. Biotechnol. Lett. 30:1879-1891.
25. Oesch, F., D. M. Jerina, and J. W. Daly. 1972. A reconstituted, microsomal enzyme system that converts naphthalene to trans-1,2-dihydroxy-1,2-dihydronaphthalene via naphthalene-1,2-oxide: presence of epoxide hydrase in cytochrome P-450 and P-448 fractions. Arch. Biochem. Biophys. 153:62-67.
26. Perrin, D. R., and I. A. M. Cruickshank. 1969. The antifungal activity of pterocarpans towards *Monilinia fructicola*. Phytochem. 8:971-978.
27. Seo, J., S.-I. Kang, M. Kim, D. Won, H. Takahashi, J. H. Ahn, Y. Chong, E. Lee, Y. Lim, R. A. Kanaly, J. Han, and H. G. Hur. 2010. Time-dependent density functional theory-assisted absolute configuration determination of cis-dihydrodiol metabolite produced from isoflavone by biphenyl dioxygenase. Anal. Biochem. 397:29-36.
28. Seo, J., S. Kang, J.-Y. Ryu, Y.-J. Lee, K. D. R. Park, Mihyang, D. Won, H.-Y. Park, J. H. Ahn, Y. Chong, R. A. Kanaly, J. Han, and H. G. Hur. 2009. Location of flavone B-ring controls regioselectivity and stereoselectivity of naphthalene dioxygenase from *Pseudomonas* sp. strain NCIB 9816-4. Appl. Microbiol. Biotechnol. in press.
29. Seto, M., K. Kimbara, M. Shimura, T. Hatta, M. Fukuda, and K. Yano. 1995. A novel transformation of polychlorinated biphenyls by *Rhodococcus* sp. strain RHA1. Appl. Environ. Microbiol. 61:3353-3358.
30. Seto, M., E. Masai, M. Ida, T. Hatta, K. Kimbara, M. Fukuda, and K. Yano. 1995. Multiple polychlorinated biphenyl transformation systems in the gram-positive bacterium *Rhodococcus* sp. strain RHA1. Appl. Environ. Microbiol. 61:4510-4513.
31. Suenaga, H., M. Goto, and Furukaw. 2006. Active-site engineering of biphenyl dioxygenase: effect of substituted amino acids on substrate specificity and regiospecificity. Appl. Microbiol. Biotechnol. 71:168-176.
32. Suenaga, H., T. Watanabe, M. Sato. Ngadiman, and K. Furukawa. 2002. Alteration of regiospecificity in biphenyl dioxygenase by active-site engineering. J. Bacteriol. 184: 3682-3688.
33. van Aardt, T. G., H. van Rensburg, and D. Ferreira. 1999. Direct synthesis of pterocarpans via aldol condensation of phenylacetates with benzaldehydes. Tetrahedron 55:11773-11786.
34. Wang, X.-L., H. G. Hur, J. H. Lee, K. T. Kim, and S.-I. Kim. 2005. Enantioselective synthesis of S-equol from dihydrodaidzein by a newly isolated anaerobic human intestinal bacterium. Appl. Environ. Microbiol. 71:214-219.
35. Wang, X.-L., K.-H. Shin, H. G. Hur, and S.-I. Kim. 2005. Enhanced biosynthesis of dihydrodaidzein and dihydrogenistein by a newly isolated bovine rumen anaerobic bacterium. J. Biotechnol. 115:261-269.
36. Won, D., B.-K. Shin, S. Kang, H. G. Hur, M. Rim, and J. Han. 2008. Absolute configurations of isoflavan-4-ol stereoisomers. Bioorg. Med. Chem. Lett. 18:1952-1957.

The invention claimed is:

1. A method for preparing pterocarpan comprising:
 (a) contacting a substrate, isoflavan-4-ol, and an enzyme, biphenyl dioxygenase to form isoflavan-4-ol-2,3-epoxide; and
 (b) forming pterocarpan from isoflavan-4-ol-2,3-epoxide;
 wherein the biphenyl dioxygenase has an amino acid sequence selected from the group consisting of SEQ ID NO:2 and SEQ ID NO:3.

2. The method of claim 1, wherein biphenyl dioxygenase is contained in bacterial cells.

3. The method of claim 2, wherein the bacterial cells are *Escherichia coli*.

4. The method of claim 2, wherein biphenyl dioxygenase is derived from *Pseudomonas pseudoalcaligenes* and has an amino acid sequence of SEQ ID NO:3.

5. The method of claim 1, wherein enantiomerically pure pterocarpan is prepared.

6. The method of claim 5, wherein the enantiomerically pure pterocarpan is one selected from the group consisting of (3S,4S)-cis-pterocarpan, (3R,4R)-cis-pterocarpan, (3S,4R)-trans-pterocarpan, and (3R,4S)-trans-pterocarpan.

* * * * *